United States Patent [19]

Dechene et al.

[11] 4,063,153
[45] Dec. 13, 1977

[54] VAPOR LIQUID FRACTION DETERMINATION

[75] Inventors: Ronald L. Dechene, Boxford; Frank G. Grimaldi; Robert E. Newton, both of Tewksbury, all of Mass.

[73] Assignee: Auburn International, Inc., Danvers, Mass.

[21] Appl. No.: 719,196

[22] Filed: Aug. 31, 1976

[51] Int. Cl.² .................................................. G01N 27/42
[52] U.S. Cl. .................................................. 324/30 R
[58] Field of Search .................. 204/DIG. 7, DIG. 9; 324/.5 B, 86, 30 R, 29; 73/205 D

[56] References Cited

U.S. PATENT DOCUMENTS 3,559,044  1/1971  Vander Heyden .................. 324/.5 B

*Primary Examiner*—M. Tokar
*Attorney, Agent, or Firm*—Jerry Cohen

[57] ABSTRACT

The relative amounts of liquid phase versus vapor phase of a mixed phase conductive fluid, such as boiling water, is determined by conductivity measurement taken in several distributed directions overlapping within the cross section of a flow path by providing a rotating field vector therein with an alternating voltage on the order of 1-30 kilohertz, with conductivity measurement produced by the rotated field being divided by a liquid conductivity measurement to determine liquid fraction (and by subtraction from unity, vapor fraction), the rotating electrical field being produced by application of a multi-phase alternating current to groups of electrodes with poled pairs distributed in alternation around the periphery of the cross section to be measured, the electrode structure and intervening insulators defining a flow measuring cross section with allowance for rigors of flow conditions and fluid environment to provide reliable, long-lived effective measurement.

11 Claims, 10 Drawing Figures

VAPOR LIQUID FRACTION DETERMINATION

BACKGROUND OF THE INVENTION

The present invention relates to measuring relative fractions of liquid and vapor in mixed phase fluid flow, such as occurs in boiling water, non-boiling turbulent flows, fluidized bed experiments, water-gas mixing analysis, nuclear plant cooling and other diverse application.

The prior art includes a number of mechanical and electrical approaches to the problem limited principally in their failure to deal effectively with the non-homogeneous character of the vapor and liquid mixture across the cross section of a conduit in most practical applications.

It is an important object of the invention to provide vapor and liquid fraction measurement in a mixed flow dealing effectively with the non-homogeneous cross-section profile of such mixtures.

It is a further object of the invention to provide a long-lived apparatus dealing with environmental conditions such as corrosive fluids, cavitation, thermal expansion and contraction and pressure in an effective way providing long life operation reliably.

It is a further object of the invention to provide a simple construction making a minimal disturbance on the system being measured consistent with one or more of the preceding objects.

It is a further object of the invention to screen out sources of spurious reading consistent with one or more of the preceding objects.

It is a further object of the invention to accommodate both measurement of relevant fluid characteristics consistent with one or more of the preceding objects.

It is a further object of the invention to provide an economical device consistent with one or more of the preceding objects.

SUMMARY OF THE INVENTION

In accordance with the invention, conductivity measurements are made in each of several current loops including conductive electrolytic paths through the cross section of the flow to be measured in distributed, but preferably overlapping array, the conductivity measurement made in each loop being summed and a rotating electrical field source supplying the loops, preferably by application of a multi-phase voltage oscillation to the loops in sequence at a rate which is high compared to the fluid flow rate so that the fluid is essentially standing still for purposes of the measurements to be summed up. A separate measurement of liquid may be made in the same fashion and divided into the summed conductivity measurements through the flow in question to compensate for bulk conductivity changes in the fluid being measured. The frequency of the field applied for conductivity measurement is preferably from 1-30 kilohertz, preferably 5 kilohertz, i.e., greater than common power frequencies and much lower than radio frequencies. Readings of conductivity are taken through high impedance connection to the flow loop and the excitation of each loop is through an isolation transformer of low ouput impedance such that changes in conductivity in the flow medium primarily control current through a loop.

The rotational electrical field is provided through multiple pairs of opposing electrodes arrayed to provide the rotating electrical field and distribution discussed above. Additionally, the electrodes and intervening insulators define a flow cross section between them. Interfaces between the electrodes and intervening insulators allow relative movement to accommodate thermal expansion and contraction differences between the electrode and insulator materials which may have greatly differing coefficients of thermal expansion and contraction, but along planes which do not cross the center of the conduit to avoid excessive loading of individual pieces. All pieces in the electrode/insulator assembly are vented to provide pressure equalization out to the inner wall surface of a pressure vessel (usually a pipe) containing them thus reducing structural requirements of the individual pieces and yielding conditions permitting the use of spring loading on the electrodes and sliding surface indexing of the array. The assembly is jam proof nowithstanding pressure and expansion/contraction requirements of its operation.

Other objects, features and advantages of the invention will be apparent from the following detailed description of preferred embodiments thereof taken in connection with the accompanying drawing, in which,

DETAILED DESCRIPTION OF THE DRAWING

Figure 1:
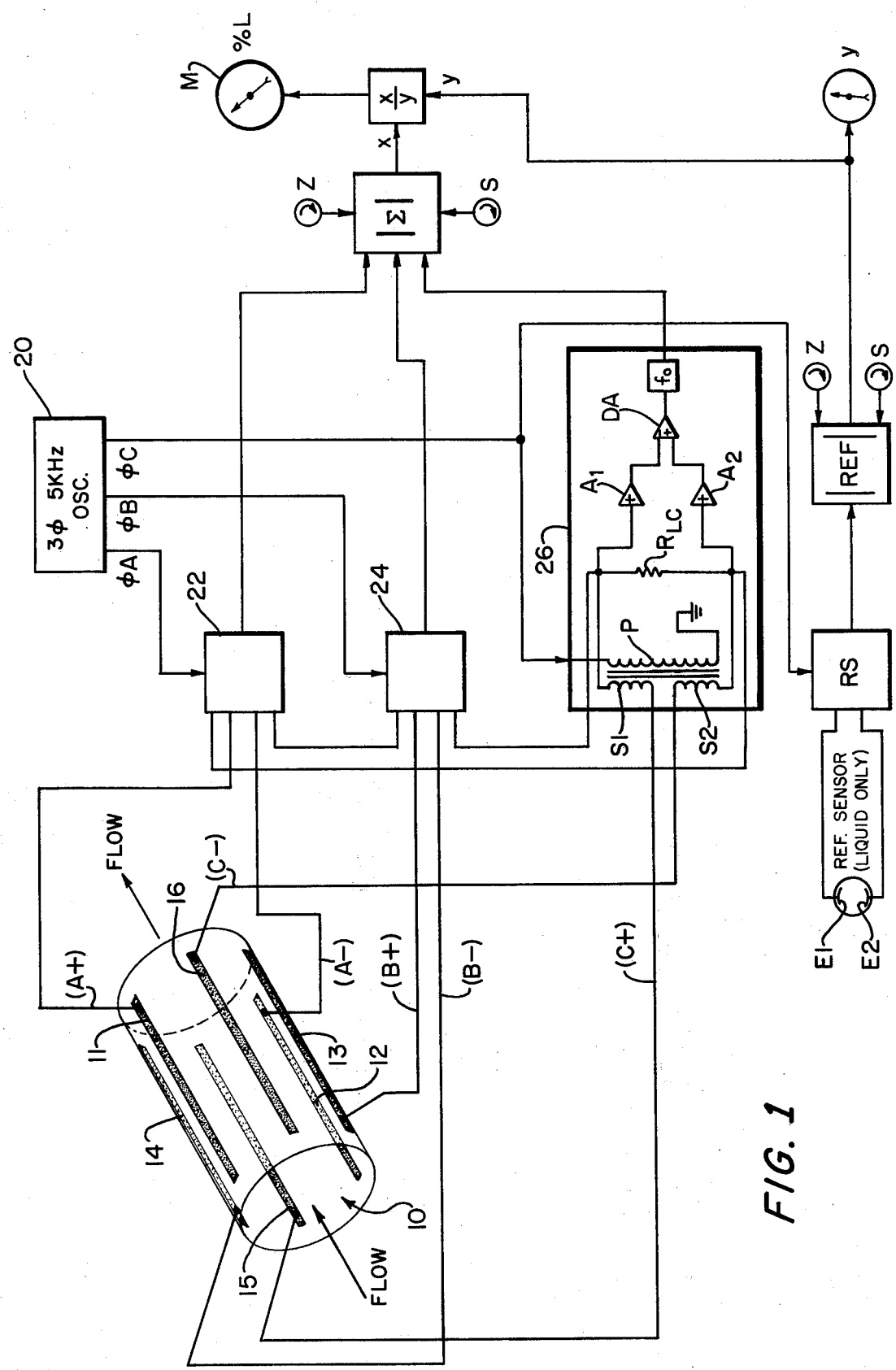
FIG. 1 is a block diagram of the measuring system in accordance with a preferred embodiment of the invention.
Figure 1A:
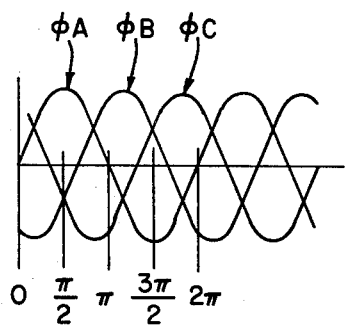
FIG. 1A is a voltage-time trace showing the phase relationship of oscillator driving signal to three sets of poled electrode pairs for the FIG. 1 embodiment.
Figure 2:
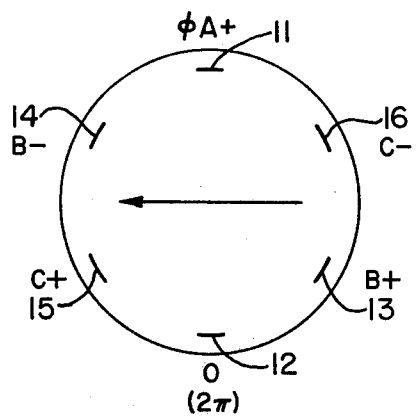
FIGS. 2–5 are cross section diagrams of the electrode array showing electric field rotation with vector positions corresponding to the positions indicated as fractions or multiples of pi radians of revolution in FIG. 1A.
Figure 3:
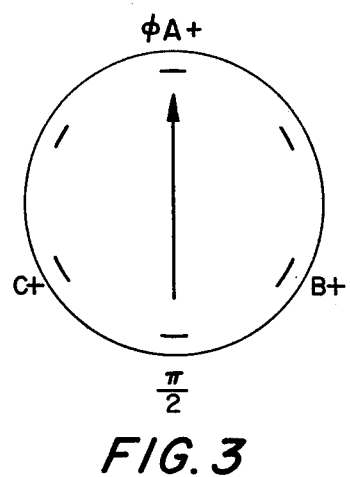
Figure 4:
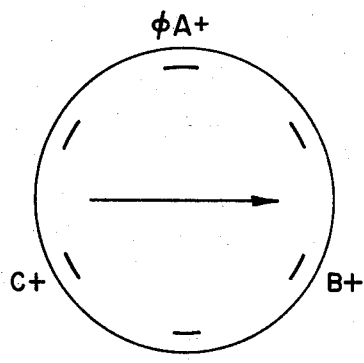
Figure 5:
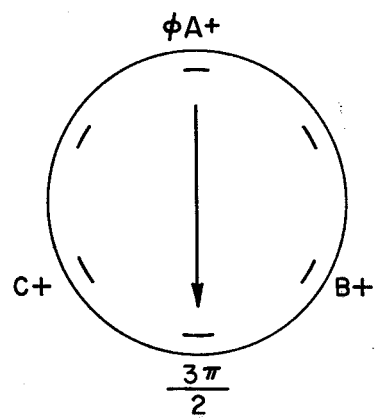
Figure 7:
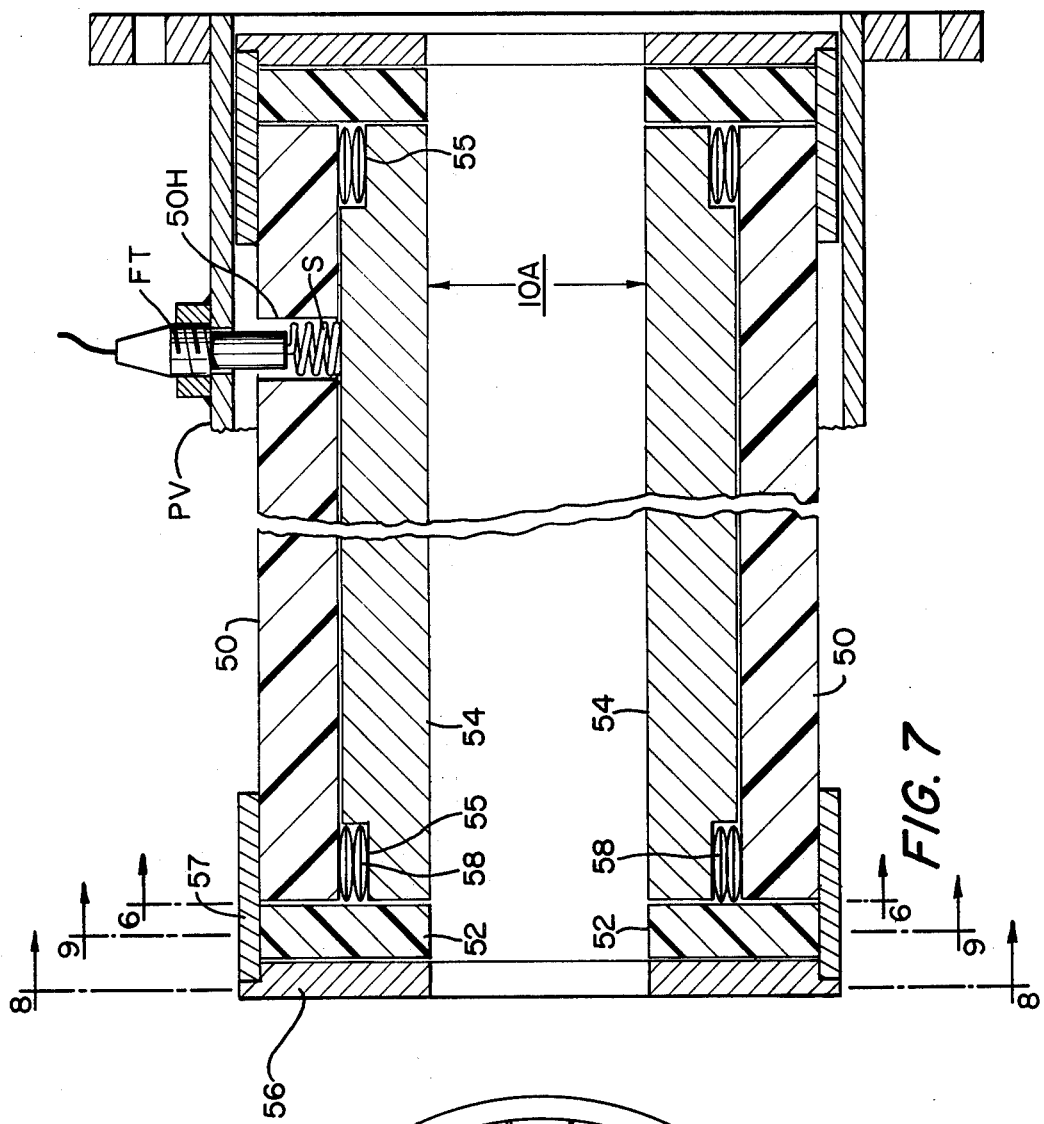

Referring now to FIG. 1, it is shown that the sensor of the invention comprises a flow conduit indicated schematically at 10 and containing therein electrodes 11–16, wired so that 11 and 12 comprise an oppositely poled pair in a first phase indicated as phase-A plus (+) and phase-A minus (−) and similar pairs are provided by electrodes 13–14 and 15–16 for phases B and C respectively. Arrows indicate the direction of flow through the conduit of liquid whose liquid/void fractions are to be determined through conduit 10. A three phase, five kilohertz oscillator indicated at 20 provides voltages to control circuits 22, 24, and 26 for phases A, B, and C respectively, the latter being indicated in greater detail, representative of all three, as comprising its plus and minus terminals for connection to the electrodes as being connected to sections S1 and S2 of the secondary windings of a transformer with a primary winding P connected to the oscillator voltage source, the secondary windings being in a series with a low impedance (preferably 5–15 ohms) resistor $R_{LC}$ (which is connected in delta circuit with the low impedance resistors $—R_{LA}$ and $R_{LB}$ (not shown)—of the other two phases).

Taps are taken on both sides of the load resistor through non-inverting amplifiers $A_1$ and $A_2$ whose outputs are connected to a differential amplifier indicated at DA and whose output is taken through a high pass filter $f_o$ to an absolute value (rectified) summing circuit $|\Sigma|$ with calibrations means Z and S which produces an output X which can be divided by a reference signal Y using a multiplier/divider (e.g., Intronics 530J four quadrant multiplier/divider or equivalent). The reference signal Y is produced by a reference control circuit RS and fed to an absolute value circuit $|REF|$ with the calibration means Z and S to provide a quotient which can be fed to a meter M to indicate percent liquid in the sensor. The quotient is established by a reference sensor located in the liquid only and which is also excited by the oscillator 20. As stated above, this compensates for changes in bulk conductivity of the fluid medium flowing through conduit 10. The reference sensor has electrodes E1, E2 (a single pair) of the same materials as the electrode pairs on the main sensor and a control circuit RS which is similar to circuits 22, 24 and 26 with the exception that its load resistor is not connected to the load resistors of the other circuits nor to any other external circuits.

The isolation transformer in each phase control circuit is of low output impedance, on the order of 10 to 15 ohms and the load resistor of each loop has a load value on the order of 10 ohms so that changes in conductivity between electrodes will primarily control the current through the loop and hence the voltage across the load resistor will represent the true conductivity between the electrodes. The isolation transformer also prevents spurious current paths through other electrodes, other sensors and power ground loops.

To insure balance of common mode paths three high value, i.e., in the order of 1 megohm, resistors (not shown) are connected from each node of the load resistor delta to ground.

The non-inverting inputs of the two operational amplifiers $A_1$ and $A_2$ are employed to provide high impedance connections (on the order of 5 to 20 megohms) to the load resistor minimizing the possibility of extraneous current paths. The outputs of the operational amplifiers A, and $A_2$ are combined by differential amplifier DA to form a signal referenced to ground. High pass filter $f_o$ combined with the high frequency rolloff characteristics of the operational amplifiers forms a band pass filter characteristic centered about the operating frequency for the system.

The operating frequency in each phase established by the three phase oscillator is about 5 kilohertz, but may be as low as 1 kilohertz or as high as 30 kilohertz. This is greatly displaced from the competing frequency operations of power equipment and radio equipment.

The operational amplifiers employed throughout the circuitry are bipolar differential input devices with high input and low ouput impedances; also they are of IC (integrated circuit) construction and are selected such that their high frequency cut-off is higher than the operating frequency.

Referring now to FIGS. 6–9, the mechanical configuration of the electrode assembly may comprise six ceramic insulator blocks of rectangular cross section and elongated lengths, indicated at 51, interspersed with hexagonal conductive electrode blocks 54 of similar elongated lengths, the latter being backed by peripheral insulating spacer elements 50 to define among them a central conduit cross-section 10A which has the same flow cross section as adjacent lengths of conduit in the system whose fluid is to be measured. The electrode-insulator array contains features for venting flow pressure forces directly to the outer pressure tube reducing structural requirements of individual internal sensor items.

End caps 56 are provided for the sensor assembly and they are separated from the electrodes 54 by end insulators 52. Assembly rings 57 mounted from the end caps hold the interlocking assembly array in place. The electrodes 54 are undercut at their ends at 55 to provide room for Belleville-spring washer stacks 58 [and stack locating dowel pins (not shown)] between 50 and 54 to force the latter inwardly until stopped by interfacial contact of inwardly converging walls 54W of 54 with the straight walls of 51 which are parallel but but coincident with radial lines from the center of the assembly. The inward convergence of the inner sidewalls of electrodes 54 is such that the convergence is not at the center of the conduit but rather short of that point to lower the loading which occurs on individual pieces. Belleville washers have the necessary force-deflection characteristics (e.g. 100 lb. force in 0.04 inches deflection) to provide the necessary loading in a small electrode assembly space.

Figure 6:
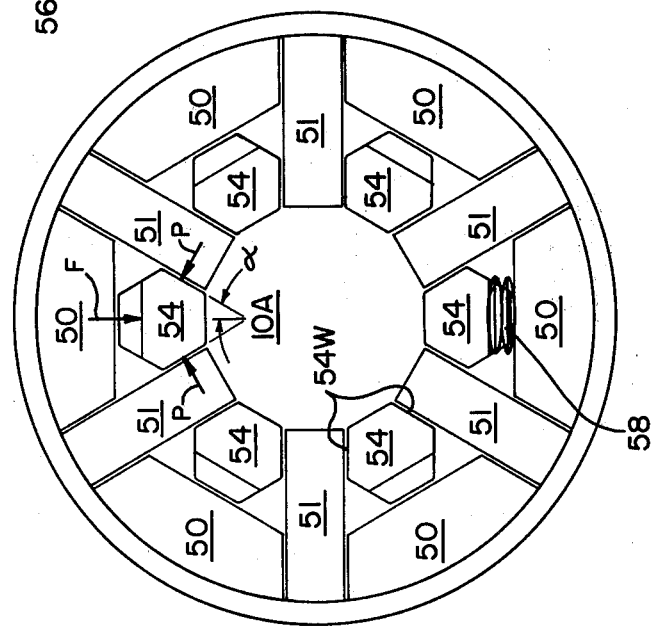
FIGS. 6, 8 and 9 are cross section views of the mechanical arrangement of an electrode assembly for the FIG. 1 embodiment taken at the locations indicated at 6—6, 8—8, and 9—9 in FIG. 7 which, is a partial longitudinal section thereof.
Figure 8:
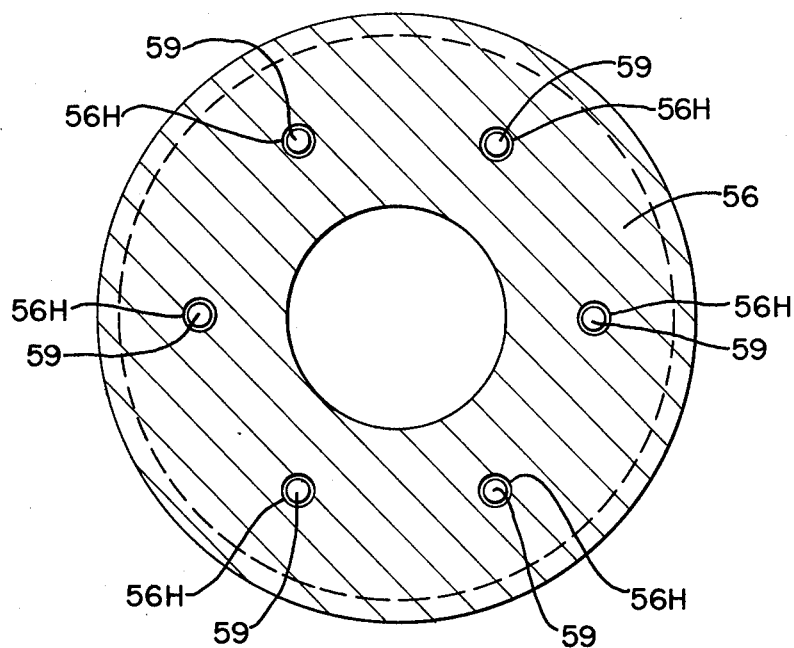
Figure 9:
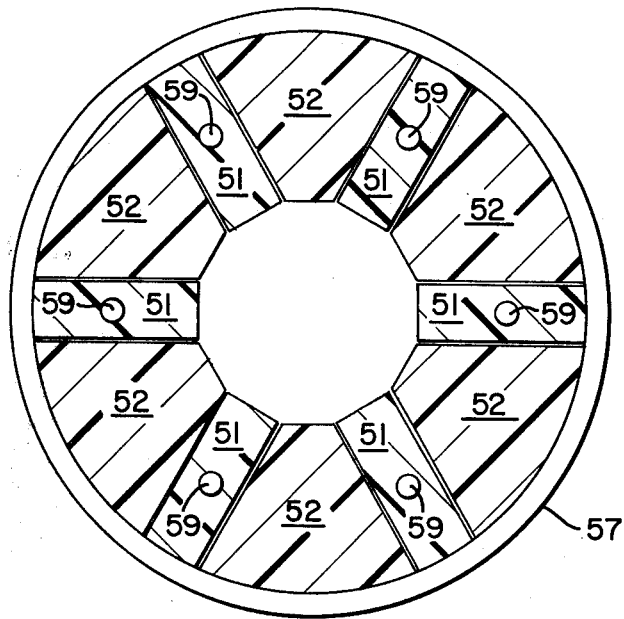

Referring to FIG. 6, a force diagram of applied spring forces F acting radially inwardly against normal reaction forces P, in cooperation with the just mentioned broad convergence angle (defined by half-angle $\alpha$) and a static coefficient of friction of $\mu$, is analyzed. For electrode 54 to retract rather than jam upon radial inward contraction of the assembly (e.g., as a result of large, rapid reductions in temperature) F must be greater than P.

The relevant force equation is:

$$F = 2P(\mu \cos \alpha + \sin \alpha)$$

For the force F to be greater than the force P, the term $(\mu \cos\alpha + \sin\alpha)$ which is a function of the friction of the electrode/insulator surfaces ($\mu$) and the half angle ($\alpha$) of the wedge section (of which the electrode represents a part) must equal 0.5 or greater.

For the expected range of friction values of possible electrode/insulator surfaces this will most readily be accomplished if the intersection of the projection of the electrode surfaces 54W for any electrode intersect at a point between the electrode and the center of the flow tube.

The back-up insulating segments 50 are of greater length than electrodes 54 by a length dimension slightly greater than is required to accommodate the difference in the thermal expansion of the two materials. Lengths of insulating segments 51 are equivalent to the distance between end caps 56 and these insulators 51 are retained by dowel pins 59 at their ends which index into holes 56H in the end caps 56 at the ends. Such holes are oversized to allow slight radial displacement of the insulators 51 to accommodate the internal pressure and pressure tube expansions due to extreme temperature conditions encountered with some flows to be measured while retaining the insulators 51 from collapsing into the flow cross section.

The materials of construction of the various components may be any conductor for electrodes which is structurally able to withstand flow environment conditions, stainless steel being preferred for boiling water applications and fused alumina being preferred for insulators in such applications. The sidewalls of the electrodes may be coated with insulating oxide by flame spraying or other methods to provide electrical insulation and limit leakage currents (e.g., to metal pressure vessel surfaces). The springs S may be surrounded by Teflon or other insulating sleeves to similarly limit leakage currents.

The electrode/insulator assembly is mounted in a pressure vessel tube PV having flanges FL. Electrical connection and feed through to outside for the six electrodes is accomplished using spark plug type ceramic feed throughs FT passing through an outer wall (one of which is shown), and also passing through holes 50H in insulator 50 and connected to the electrodes by means of helical compression spring conductors S. The pairs of connector springs S are longitudinally offset. For insertion or removal of the assembly into or from PV, springs S and feedthroughs FT are retracted.

The Belleville stack configurations are determined by specific loading and deflection requirements of a fluid line. Similarly, helical compression spring connections S to electrodes 54 are determined by such characteristics. The number and length of electrodes can vary based on electrical and spatial considerations for a specific application. In general, the electrode length must be such in relation to fluid flow rate that the measurements can be taken as though the fluid was standing still, in effect. When the number of electrodes is other than six and when the shape of the electrodes has cross sections other than hexagonal used, the maintenance of sliding surfaces between electrodes and insulators whose planes are non-concentric with the flow of pressure to the center and a compliance electrode/insulator array will provide equivalent or almost equivalent parameter and performance, with respect to the preferred embodiment described above.

It is evident that those skilled in the art, once given the benefit of the foregoing disclosure, may now make numerous other uses and modifications of, and departures from the specific embodiments described herein without departing from the inventive concepts. Consequently, the invention is to be construed as enbracing each and every novel feature and novel combination of features present in, or possessed by, the apparatus and techniques herein disclosed and limited solely by the scope and spirit of the appended claims.

What is claimed is:

1. Method of determining liquid and vapor fractions in a non-homogeneous conductive fluid flowing through an elongated conduit with a flow axis comprising,
    establishing a moving electric field vector through application of polyphase alternating electrical field excitation to the fluid by direct contact to create distributed but crossing alternating current loci across the cross section of the conduit on a cyclic repeating basis,
    measuring and summing the magnitudes of such currents to produce a conductivity signal representative of the liquid and vapor fractions of fluid flowing through the conduit.

2. Method in accordance with claim 1 wherein a separate single phase reference conductivity measurement is made, in the liquid fraction only, to compensate bulk conductivity changes.

3. Apparatus for measuring liquid and vapor fraction in a fluid in accordance with claim 1 comprising,
    plural means for establishing conductive loops including the fluid and a load resistor,
    the loops being overlapped and distributed within the conduit cross section,
    each such loop being excited by an alternating voltage source out of phase with the alternating voltage source of other loops to establish a moving field vector.

4. Measuring apparatus in accordance with claim 3 wherein there are three loops, each of which comprises two opposing elongated electrodes defining a flow conduit with a flow axis,
    the electrode pairs being located on diameters of said conduit and extending longitudinally parallel to the flow axis of the conduit.
    and an isolation transformer means for exciting each loop,
    the load resistors of the three loops being arranged in a delta circuit and each such load resistor of each loop being placed between halves of the divided secondary of said isolation transformer of the loop.

5. Measuring apparatus in accordance with claim 4 and further comprising differential amplifier conductivity measuring means for minimizing extraneous current paths.

6. Measuring apparatus in accordance with claim 3 and further comprising insulating spacers peripherally intermediate with the electrodes,
    and wherein the electrodes together with said intermediate insulating spacers form a flow passage outer surface.

7. Measuring apparatus in accordance with claim 6 wherein the electrodes have hexagonal cross section configurations and the intervening insulators are long rectangles in cross section leaving dead radial space behind each electrode,
    further insulator means in said dead spaces having lengths substantially the same as the electrodes,
    the insulator arrangement being pinned and the electrode-insulator array being configured to prevent inward collapse and accommodating thermal expansion and contraction difference between electrodes and insulators through sliding motion along interface planes which do not intersect the flow passage center but interact short thereof.

8. Measuring apparatus in accordance with claim 7 wherein the electrodes are contacted by radially external spring contact members and load Belleville washer stacks by their outward expansion.

9. Measuring apparatus in accordance with claim 8 and further comprising means defining a pressure vessel with said spring contacts being anchored on the pressure vessel.

10. Method in accordance with claim 1 wherein three poled pairs of electrodes at 120° electrical phase differences are provided in circular array and excited from a common voltage source at 1–30 kilohertz.

11. Method of determining liquid and vapor fractions in accordance with claim 2 wherein a rotating electric field vector is established.

* * * * *